United States Patent [19]

Kumar

[11] Patent Number: 4,500,657
[45] Date of Patent: Feb. 19, 1985

[54] DENTAL RESTORATIVE COMPOSITIONS HAVING IMPROVED MECHANICAL PROPERTIES AND HYDROLYTIC STABILITY

[75] Inventor: Narayan G. Kumar, Freehold, N.J.

[73] Assignee: Johnson & Johnson Dental Products Company, East Windsor, N.J.

[21] Appl. No.: 509,770

[22] Filed: Jul. 1, 1983

Related U.S. Application Data

[63] Continuation-in-part of Ser. No. 404,262, Aug. 2, 1982, abandoned.

[51] Int. Cl.³ ............................................. A61K 5/06
[52] U.S. Cl. .................................... 523/116; 523/117; 204/159.23
[58] Field of Search .................... 523/116; 260/998.11

[56] References Cited

U.S. PATENT DOCUMENTS

| 3,808,170 | 4/1974 | Rogers | 260/998.11 |
|---|---|---|---|
| 3,923,740 | 12/1975 | Sohmik et al. | 106/35 |
| 3,926,906 | 12/1975 | Lee et al. | 523/116 |
| 4,071,424 | 1/1978 | Dart et al. | 204/159.15 |
| 4,110,184 | 8/1978 | Dart et al. | 523/116 |
| 4,192,795 | 3/1980 | Madhavan et al. | 260/998.11 |
| 4,220,582 | 9/1980 | Orlowski et al. | 523/116 |
| 4,222,835 | 9/1980 | Dixon | 204/159.18 |
| 4,292,029 | 9/1981 | Craig et al. | 523/276 |
| 4,297,266 | 10/1981 | Ibsen et al. | 523/116 |
| 4,302,376 | 11/1981 | Walkowiak et al. | 525/308 |
| 4,350,532 | 9/1982 | Randklev | 106/30 |
| 4,407,984 | 10/1983 | Ratcliffe et al. | 523/116 |
| 4,431,421 | 2/1984 | Kawahara et al. | 523/116 |

Primary Examiner—Herbert J. Lilling
Attorney, Agent, or Firm—Charles J. Metz

[57] ABSTRACT

There is disclosed a dental restorative composition containing a hydrophobic polymerizable composition, a polymerization initiator, and a quartz or heat treated barium or strontium glass hydrophobic filler having an average particle size below 15 microns, with said filler being present in an amount within the range of from about 35 to about 78 volume percent.

20 Claims, No Drawings

DENTAL RESTORATIVE COMPOSITIONS HAVING IMPROVED MECHANICAL PROPERTIES AND HYDROLYTIC STABILITY

This application is a continuation-in-part of my copending application Ser. No. 404,262, filed Aug. 2, 1982 and now abandoned.

The invention relates to a dental restorative composition having improved mechanical properties and hydrolytic stability.

BACKGROUND OF THE INVENTION

Dental restorative compositions comprising a polymerizable resinous composition plus a filler are finding wide acceptance in the practice of dentistry. An illustration of such compositions is the dental filling material described by Lee et al. in U.S. Pat. No. 3,539,533. However, such resin based dental filling materials have found limited use for the filling of cavities on the grinding surfaces of molars. The reason for this is that such compositions have been found to have inadequate wearing properties to withstand the stresses which are normal in such areas. Among the factors that contribute to the inadequate wear properties of the prior art resinous dental restorative dental compositions are microfractures of the overall composite and debonding that occurs at the filler/polymer matrix interface. Both of these are most likely to occur during the cyclic loads encountered while chewing in an aqueous environment, with modest temperature fluctuations. Inadequate hydrolytic stability appears to contribute to both the microfractures and debonding. The present invention is directed to a dental restorative composition that substantially improves hydrolytic stability, resistance to debonding at the filler/polymer interface, and resistance to the formation and propagation of microfractures in the composite.

BRIEF SUMMARY OF THE INVENTION

The invention provides a dental restorative dental composition that consists essentially of the following three components:

(a) a polymerizable composition containing at least one compound having at least two olefinically unsaturated groups, wherein, when said polymerizable composition is polymerized in the unfilled state, the resulting cured material has a water absorption as determined by ADA Specification No. 27 at 37° C. for one week, of less than 1 milligram per square centimeter;

(b) a polymerization initiator for said polymerizable composition; and (c) a particular hydrophobic inorganic filler having at least 30 percent of the particles and preferably at least 70 to 100 percent of the particles less than 5 microns, with a corresponding volume average particle size not more than 15 microns and preferably not more than 5 microns, said filler being present in an amount within the range of from about 35 to about 78 volume percent, based on volume of said polymerizable composition plus said filler.

In a preferred aspect, the composition of the invention contains from about 5 to about 30 weight percent of colloidal silica, the percentage being based upon the weight of the entire dental restorative composition.

THE PRIOR ART

Dental restorative compositions that include a polymerizable resinous compound free of active hydrogen have been disclosed. For instance, see Orlowski et al., U.S. Pat. No. 4,220,582, who disclose the use of the dimethacrylate of ethoxylated bisphenol-A and polyethylene glycol dimethacrylate in dental restorative compositions.

The use in dental restorative compositions of hydrophobic fillers such as quartz has been disclosed. For instance, see Schmitt et al. in U.S. Pat. No. 3,923,740.

Ibsen et al., in U.S. Pat. No. 4,297,266, disclose dental restorative compositions containing "hydrophobic" colloidal silica and 2 to 30 micron glass particles as fillers. Among the resins disclosed are ethyoxylated bisphenol-A dimethacrylate and triethylene glycol dimethacrylate.

Dixon, in U.S. Pat. No. 4,222,835, teaches polymerizable compositions (for coatings or fiber glass-reinforced materials) containing a wide variety of acrylic esters.

Lee et al., in U.S. Pat. No. 4,032,504, disclose dental restorative compositions including a filler having a particle size of from 0.5 to about 50 microns, with an average particle size of from about 2 to about 15 microns.

Ibsen et al., in U.S. Pat. No. 4,297,266, disclosed dental restorative compositions containing glass particles and a hydrophobic silica filler.

Rossi, in U.S. Pat. No. 3,792,531, contains a similar disclosure. Dental restorative compositions containing sub-micron size fillers have also been disclosed. For instance, see Australian Pat. No. 484,167.

DETAILED DESCRIPTION OF THE INVENTION

In its broadest aspect, the invention provides a means to obtain a combination of a number of desirable features. First, the polymerizable compositions employed in the invention are relatively hydrophobic when cured, which enhances the hydrolytic stability of the restorative compositions. Second, relatively hydrophobic and chemically durable fillers are employed in order to provide additional resistance to hydrolytic attack at the filler/polymer matrix interface. And third, the use of small filler particles at relatively high filler loadings decreases the interparticle spacing in the cured composite which results in an increased number of obstacles to the propagation of small cracks initiated by defects in the system such as voids. In preferred aspects of the invention, the number of voids in the cured composite are reduced by employing relatively low viscosity resinous compounds, and/or by mixing the paste system under vacuum and preserving the resultant low void content by the use of a single component photocured system.

The various components of the invention, which are described more fully below, are employed for the purpose of achieving the above described features of the invention.

The polymerizable composition that is employed as the polymer matrix in the invention is a compound that has at least two olefinically unsaturated groups and which is relatively hydrophobic when cured, as is evidenced by low water absorption. One way to obtain the desired hydrophobic properties is to employ polymerizable compounds that are free of active hydrogen. By "active hydrogen" is meant the hydrogen contained in groups such as hydroxyl, carboxyl, primary or secondary amino, amido, sulfhydryl, and the like. (A convenient test for such active hydrogen groups is that they react with isocyanate in the presence of tertiary amine catalyst.) A wide variety of such compounds can be employed. They include alkoxylated bisphenol-A acrylates or methacrylates, alkane diol acrylates or methacrylates, polyalkylene glycol acrylates or methacrylates, and the like. The preferred compounds are the $C_4$-$C_{12}$ alkane diol acrylates or methacrylates such as 1,10-decamethylene diol dimethacrylate and 1,6-hexamethylene diol dimethacrylate, and ethoxylated bisphenol-A dimethacrylate. The nature and preparation of such compounds are known in the art.

The dental restorative composition of the invention includes a polymerization initiator. Such initiators are known in the art and can be used in their customary proportions. For instance, the composition can be divided, one package containing a peroxide such as benzoyl peroxide, and the other containing an activator for the peroxide such as N,N-di-(2-hydroxyethyl)-p-toluidene. Other initiator systems known in the art can also being used.

In order to minimize the formation of voids, in a preferred aspect of the invention, the initiator is a photosensitive initator system so that the mixing step necessary for the two-component, self-curing composite systems can be avoided. In this aspect, a one-package system is used. Resin, filler, and the photosensitive initiator system are mixed under a vacuum to reduce void formation. The composition then needs no further mixing by the dentist or dental technician. Such photosensitive initiator systems include benzoin, benzoin ethers and esters, 2,2-diethoxy acetophenone, and the diketone compounds plus a reducing agent that are disclosed by Dart et al., in U.S. Pat. No. 4,071,424. Specific examples of preferred photoinitiator systems include benzil and/or camphoroquinone plus N,N-dimethylaminoethyl methacrylate or ethyl 4-(N,N-dimethylamino-)-benzoate.

The filler employed in the invention has a volume average particle size below 15 microns, and preferably, below 5 microns. Thirty percent of the filler particles, and preferably 70 to 100 percent, have a size below 5 microns. The filler is employed in an amount within the range of from about 35 to about 78 volume percent, based on the volume of the filler plus the polymerizable composition. Thus, the filler is employed in relatively high proportions. A volume percent of 35 to 78 corresponds approximately to 50 to 95 weight percent of the dental restorative composition of the invention, depending on the specific gravity of the filler.

The hydrophobic, chemically durable fillers that are used are quartz and/or a particular heat-treated barium or strontium glass. The hydrophobic fillers will absorb less than 0.1 weight percent water (prior to addition of silane coupling agent) when exposed to normal ambient conditions. Water content of the filler is determined by a differential scanning calorimeter ("DSC"). The first departure from baseline in a DSC scan is caused by the presence of water. To determine the amount present, the area under the peak is determined and normalized relative to the weight of the sample.

The barium or strontium glass that may be employed as the filler is selected for chemical durability, as is evidenced by resistance to leaching in an aqueous environment. Such glasses are substantially free of alkali metal oxides, and are single phase glasses. If the mole percent of barium or strontium oxide exceeds a certain point, the glass becomes two-phased. This proportion can vary, depending upon the presence and proportion of other metal oxides in the glass. For one preferred type of glass that is composed of oxides of barium, silicon, boron, and aluminum, the upper limit for a single phase glass is about 20 mole percent barium oxide. One preferred glass for use in the invention has the following composition:

$SiO_2$—67 mole percent
$BaO$—16.4 mole percent
$B_2O_3$—10 mole percent
$Al_2O_3$—6.6 mole percent.

The essential ingredients in the glass are the oxides of barium and/or strontium and silicon. Oxides of other metals such as aluminum and boron may also be present so long as such oxides do not detract from the chemical durability of the glass. Thus, significant quantities of alkali metal oxides should be avoided because, as is well known, alkali metal ions are quite soluble in aqueous media, and therefore will reduce the chemical durability of the glass. The minimum barium and/or strontium content of the glass is preferably that which is sufficient to impart X-ray opacity to the glass.

The barium and/or strontium glass powder used in the invention is acid washed and then subjected to a heat treatment to enhance its resistance to attack by water. The procedures are the following:

The acid-washing treatment to which the glass powder is subjected is carried out by known procedures. For instance, a mixture of 1 part (by weight) of glass powder, 1 part of 37 percent aqueous hydrochloric acid, and 1 part of de-ionized water is stirred at room temperature for 45 minutes, filtered, and rinsed with de-ionized water until the pH of the filtrate is the same as the rinse water. The powder is then dried at about 50° C. overnight in a forced air oven. The acid wash is used to remove metal impurities from the glass, and to reduce the amount of leachable barium or strontium from the surface of the glass.

The acid-washed glass powder is subjected to a heat treatment to reduce the affinity of the glass powder for water. This heat treatment is carried out at an elevated temperature below the sintering temperature of the glass powder (the sintering temperature can be determined by known procedures, as by thermo-mechanical analysis "TMA"), but high enough to cause a significant reduction in the specific surface area of the glass powder, as measured by known procedures such as by a "Quantasorb" B.E.T. surface area analyzer. The reduction in specific surface area will usually be at least 50 percent (i.e., the surface area of the heat treated glass powder will be less than about one-half that of the untreated powder), up to 80 to 90 percent, or even more in some cases. The heat treatment time is not at all critical in that it need be carried out only for the minimum time needed to heat all the powder to the desired temperature. Apparently the effect of the heat on the glass powder is quite rapid, and all that is required is to bring all of the mass of powder up to the desired temperature. However, since the glass powder is an excellent heat insulator, this can take several hours for masses of powder wherein the heat must travel through a significant thickness of powder to heat all of the glass to the desired temperature.

The following is an illustration of a preferred heat treatment carried out on the barium glass used below in the Examples, and referred to as Filler A or Filler B:

The barium glass had the following composition:

SiO$_2$—67 mole percent
BaO—16.4 mole percent
B$_2$O$_3$—10 mole percent
Al$_2$O$_3$—6.6 mole percent.

The raw glass powder, prior to acid wash, has a specific surface area of about 0.8±0.1 m$^2$/gm. After acid-washing as described above, the specific surface area is about 10±2 m$^2$/gm.

Five kilograms of the acid-washed powder are placed in a saggar crucible. The crucible is cylindrical, about 12 inches in diameter and 10 inches high. Five kilograms of the powder nearly fill the crucible. The crucible containing the powder is placed in an oven, which is set at 650° C. It takes about 16 hours for the entire mass of powder to heat up to 650° C. After 16 hours, the furnace is turned off and the powder is slowly cooled to room temperature. The specific surface area of the heat treated glass is about 3.5±1 m$^2$/gm.

As is known in the art, a silane coupling agent can be employed to enhance the bond between the filler and the resin. Such coupling agents include gamma-methacryloxypropyltrimethoxysilane.

It is desirable to include a small percentage of colloidal silica in the composition in order to adjust the viscosity and the handling characteristics of the composite paste. For instance, from about 2 to about 25 weight percent of colloidal silica, based on weight of the entire composite, is beneficial.

The colloidal silica is preferably treated with a silane coupling agent such as gamma-methacryloxypropyltrimethoxysilicone ("A-174"). After such treatment, the silica should be protected from ambient moisture because it may absorb up to about 1 weight percent of water from the atmosphere, as measured by DSC.

In the examples, the following materials were used:
Bisphenol-A dimethacrylate ("BADM")
Ethoxylated bisphenol-A dimethacrylate ("EBDM")
Methacrylic acid ("MAA")
1,6-hexamethylene glycol dimethacrylate ("HMGDM")
2,2'-propane bis[3-(4-phenoxy)-2-hydroxypropyl-1 methacrylate] ("Bis-GMA")
Tetraethylene glycol dimethacrylate ("TEGDM")
2-(N,N-dimethylamino)ethyl methacrylate ("DMAEMA")
Ethyl 4-(N,N-dimethylamino)benzoate ("EDMAB")
Filler A—Conventional acid-washed 0-3μ barium glass powder having the following particle size analysis (by Coulter Counter):
100% below 13μ
55% below 5μ
18% below 2μ
Water content, by DSC, was 1.05 weight percent.
Filler B—Same 0-13μ glass powder as Filler A, but heated to 650° C. for sixteen hours as described above. The water content, by DSC, was 0.05 weight percent.
Filler C—Quartz powder (0-90μ) having the following particle size analysis:
100% below 80-100μ
50% below 13μ
16% below 5μ.
The water content, by DSC, is below 0.01 weight percent.
Filler D—Quartz powder (0-10μ) having the following particle size analysis:
100% below 10μ
77% below 5μ
23% below 2μ
Water content, by DSC, is below 0.01 weight percent.
Filler E—0-90μ Barium glass powder heat treated at 650° C. for 16 hours, having the following particle size analysis:
100% below 80-100μ
50% below 13μ
12% below 5μ.
Water content, by DSC, is 0.025 weight percent.
Filler F—0-5μ Quartz powder having the following particle size analysis:
100% below 5μ
70% below 1μ
Average—0.66μ.
Water content, by DSC, was 0.01 weight percent.

The water contents are determined on the fillers prior to treatment with silane. The quartz fillers were treated with 3.2 weight percent A-174 silane (Union Carbide), and the barium glass fillers were treated with 1 weight percent A-174 silane (gamma-methacryloxypropyltrimethoxysilane).

EXAMPLES 1-2 AND CONTROLS 1-3

A series of filled resin systems, formulated to be useful as dental composites, were prepared. The composite formulations were prepared by mixing fillers into the resins using a mini-Hobart (drill) mixer until a smooth paste resulted. The pastes were then placed in a vacuum oven and de-gassed at about 4 mm. mercury pressure until they were void-free, as determined by microscopic examination. Flexural test samples were made by placing the uncured filled resins in "Teflon" molds between glass slides, and exposing each side to 60 seconds exposure from a 75 watt/12 volt quartz projector lamp. All samples were aged for 24 hours at 37° C. in deionized water. Ten samples of each composite were tested for initial flexural strength, and ten additional samples were placed in pressure bottles with 300 ml. of deionized water, and were held at about 5 atmospheres and 145° C. for 7 days. After this time, they were removed from the bottles and tested for flexural strength, using an Instron HP-11 stress-strain testing apparatus.

Table I displays the formulations and Table II displays the results of the flexural testing.

TABLE I

| | Parts by weight |
|---|---|
| Resin A | |
| Bis-GMA | 61.2 |
| BADM | 6.8 |
| TEGDM | 26.9 |
| MAA | 2.0 |
| Benzil | 0.3 |
| Camphorquinone | 0.3 |
| DMAEMA | 2.5 |
| Viscosity - 2560 cps | |
| Water Absorption[1] - 2.34 mg/cm$^2$ (0.01)[2] | |
| Resin B | |
| EBDM | 96.9 |
| Camphorquinone | 0.3 |
| Benzil | 0.3 |
| DMAEMA | 2.5 |
| Viscosity - 2240 cps | |
| Water Absorption - 0.41 mg/cm$^2$ (0.01) | |
| Resin C | |
| EBDM | 84.55 |
| HMGDM | 12.6 |
| Camphorquinone | 0.25 |
| DMAEMA | 2.5 |
| Viscosity - 1960 cps | |
| Water Absorption - 0.80 mg/cm$^2$ | |
| Control 1 | |

TABLE I-continued

| | Parts by weight |
|---|---|
| Resin A | 28 |
| Filler A | 72 |
| Control 2 | |
| Resin A | 28 |
| Filler B | 72 |
| Control 3 | |
| Resin B | 28 |
| Filler A | 72 |
| Example 1 | |
| Resin B | 28 |
| Filler B | 72 |
| Example 2 | |
| Resin C | 28 |
| Filler B | 72 |

[1] The water absorption was determined on the cured, unfilled resins by ADA Specification No. 27 - immersion in water at 37° C. for seven days.
[2] The numbers in parentheses after the test data are the standard deviations.

TABLE II

| Composite | Flexural Strength | | | Water Absorption[3] mg/cm$^2$, 7 days at 37° C. |
|---|---|---|---|---|
| | Initial Strength (N/mm$^2$) | Pressure Boiled 7 days | % Loss | |
| Control 1 | | | | |
| (hydrophilic resin) | 111.0 | 30.4 | 72.6 | 1.23 |
| (hydrophilic filler) | (13.4) | (7.9) | | (0.03) |
| Control 2 | | | | |
| (hydrophilic resin) | 108.3 | 46.4 | 56.2 | 1.07 |
| (hydrophobic filler) | (10.6) | (8.9) | | (0.03) |
| Control 3 | | | | |
| (hydrophobic resin) | 109.6 | 66.7 | 39.1 | 0.44 |
| (hydrophilic filler) | (13.7) | (9.9) | | (0.03) |
| Example 1 | | | | |
| (hydrophobic resin) | 111.6 | 78.6 | 29.6 | 0.29 |
| (hydrophobic filler) | (10.7) | (9.9) | | (0.02) |
| Example 2 | | | | |
| (hydrophobic resin) | 109.2 | 91.4 | 16.3 | — |
| (hydrophobic filler) | (13.2) | (9.2) | | |

[3] Water absorption on the filled composites.

Controls 1, 2, and 3, each of which contained either a hydrophilic resin or a hydrophilic filler or both, had much lower retention of flexural strength after pressure boiling, than did Examples 1 and 2, which exemplify the invention.

EXAMPLE 3

To illustrate the effect of particle size, 28 parts, by weight, of Resin B was mixed with 72 parts of Fillers C, D, E, and B, respectively. The composites were vacuum degassed and made into flexural test samples, as was described in Example 1. The flexural strengths were determined after aging for 24 hours in deionized water at 37° C. The results are displayed in Table III:

TABLE III

| Filler | Flexural Strength N/mm$^2$ |
|---|---|
| C (0–90μ quartz) | 117.4 (8.7) |
| D (0–10μ quartz) | 124.3 (11.7) |
| E (0–90μ Ba glass) | 108.1 (7.3) |
| B (0–13μ Ba glass) | 119.1 (7.7) |

EXAMPLES 4 AND 5

Two photocurable compositions designed for use as dental composites were made from the following formulations (Table IV):

TABLE IV

| | Parts, by Weight |
|---|---|
| Example 4 | |
| Resin B | 22.2 |
| Filler D | 66.8 |
| Colloidal Silica[4] | 11.0 |
| Example 5 | |
| Resin B | 21.6 |
| Filler B | 67.5 |
| Colloidal Silica[4] | 10.9 |

[4] Fumed silica treated with gamma-methacryloxypropyl trimethoxysilane. (Cab-O-Sil "M-5", Cabot Corporation)

The compositions were vacuum degassed and cured by exposure to light, as described in Example 1.

Representative properties of these materials after curing as described in Example 1 are shown in Table V:

TABLE V

| | Example | |
|---|---|---|
| | 4 | 5 |
| Compressive Strength, N/mm$^2$ | 354.1 | 357.7 |
| Diametral Tensile Strength, N/mm$^2$ | 64.9 | 61.4 |
| Flexural Modulus, N/mm$^2$ | 10,956 | 9,650 |
| Flexural Strength, N/mm$^2$ | 126.1 | 127.9 |
| Rockwell F Hardness | 93 | 94 |
| Water Absorption, % | 0.38 | 0.32 |
| Translucency | passes ADA spec 27 | |
| Flexural Strength, N/mm$^2$ after pressure boiling 7 days at 145° C. and 5 atmospheres | 86 (32% loss) | 117 (8% loss) |

To demonstrate the benefit of vacuum degassing to reduce voids, samples of the same formulations were cured without having been vacuum degassed, and were tested for flexural strength as described above in Example 1. The results were:

| Example 4 | 99.5 N/mm$^2$ |
|---|---|
| Example 5 | 90.8 N/mm$^2$ |

EXAMPLE 6

The following dental composite formulation was prepared:

TABLE VI

| COMPONENT | PARTS, BY WEIGHT |
|---|---|
| EBDM | 17.71 |
| dl-camphoroquinone | 0.05 |
| Benzil | 0.024 |
| EDMAB | 0.216 |
| Resin | 18.000 |
| Filler F | 62 |
| Colloidal Silica[5] | 20 |

[5] "OX-50", marketed by DeGussa: It is a fumed silica having a surface area of 50 m$^2$/gm and an average particle size of 0.05 μ. It is treated with 10 weight percent A-174 silane and has a water absorption content, by DSC, after such treatment of 0.7–0.8 weight percent.

The composite was prepared by the following procedure:

The resin is charged to a Hobart mixer, and the quartz and silica are added in six equal portions, with mixing, over a period 1½ hours. The mixture is then charged to a double planetary mixer, which is kept at an absolute pressure of 65 millimeters of mercury. The agitators in this mixer are run for about 20 seconds every 15 minutes; the mixture is kept in the mixer for 1¼ hours.

Samples were cured by exposure to light, as described in Example 1. The following physical properties were measured on the cured composite:

TABLE VII

| | | |
|---|---|---|
| Compressive Strength, N/mm² | 340 | (49,000 psi) |
| Diametral Tensile Strength, N/mm² | 67.6 | (9,880 psi) |
| Flexural Modulus, N/mm² | 17,500 | |
| Flexural Strength, N/mm² | 134 | |
| Rockwell F Hardness | 101.2 | |
| Translucency | Passes ADA SPEC 27 | |

In a dental composite, one of the important physical properties that has an effect on durability is flexural modulus. The flexural modulus of natural tooth enamel is of the order of 50,000 to 80,000 N/mm². Where there is a large difference between the flexural moduli of natural enamel and the restoration, significant stresses can be encountered at the enamel/restoration interface.

One of the reasons that polymer-based dental composites may not function well in Class 2 restorations (i.e., on biting surfaces of molars) is the large disparity between their flexural moduli (which can be as low as 7000 N/mm²) and that of natural tooth enamel. While the inventor herein has observed isolated batches of conventional composite material whose flexural moduli have approached that of this Example 6, preferred embodiments of the restorative compositions of this invention are the first composite formulations that the inventor has seen whose properties, including flexural modulus, are consistently such that they are legitimate candidates for clinical evaluation as Class 2 restorative materials.

What is claimed is:

1. A dental restorative composition consisting essentially of:
   (a) a polymerizable composition containing at least one compound having at least two olefinically unsaturated groups, wherein, when said polymerizable composition is polymerized in the unfilled state, the resulting cured material has a water absorption as determined by ADA Specification No. 27 at 37° C. for one week, of less than 1 milligram per square centimeter;
   (b) a polymerization initator for said polymerizable composition; and
   (c) a hydrophobic inorganic filler having a volume average particle size below 15 microns, at least 30 percent of the particles of said filler having a size of less than 5 microns, said filler being present in an amount within the range of from about 35 to about 70 volume percent, based on weight of said polymerizable composition plus said filler, and said filler being selected from the group consisting of quartz and acid-washed and heat treated barium or strontium glass, wherein the heat treatment is carried out at a temperature below the sintering temperature of the glass, and at a temperature and for a period of time sufficient to effect at least a 50 percent reduction in the specific surface area of the glass.

2. The dental restorative composition of claim 1 wherein said component (a) is at least one compound selected from the group consisting of $C_4$–$C_{12}$ alkanediol acrylate or methacrylate and alkoxylated bisphenol-A acrylate or methacrylate.

3. The dental restorative composition of claim 1 wherein said component (a) includes ethoxylated bisphenol-A dimethacrylate.

4. The dental restorative composition of claim 1 wherein said component (a) includes 1,10-decamethylene diol dimethacrylate or 1,6-hexamethylene diol dimethacrylate.

5. The dental restorative composition of claim 3 wherein said component (a) includes 1,10-decamethylene diol dimethacrylate or 1,6-hexamethylene diol dimethacrylate.

6. The dental restorative composition of claim 1 wherein said composition includes colloidal silica.

7. The dental restorative composition of claim 5 wherein said composition includes colloidal silica.

8. The dental restorative composition of claim 1 wherein said hydrophobic inorganic filler is quartz.

9. The dental restorative composition of claim 2 wherein said hydrophobic inorganic filler is quartz.

10. The dental restorative composition of claim 1 wherein said hydrophobic inorganic filler is heat treated barium glass.

11. The dental restorative composition of claim 2 wherein said hydrophobic inorganic filler is heat treated barium glass.

12. The dental restorative composition of claim 1 wherein said polymerization initiator is photosensitive.

13. The dental restorative composition of claim 2 wherein said polymerization initiator is photosensitive.

14. The dental restorative composition of claim 5 wherein said polymerization initiator is photosensitive.

15. The dental restorative composition of claim 6 wherein said polymerization initiator is photosensitive.

16. The dental restorative composition of claim 8 wherein said polymerization initiator is photosensitive.

17. The dental restorative composition of claim 10 wherein said polymerization initiator is photosensitive.

18. The composition of claim 10 wherein the heat treated barium glass has the following approximate composition:
$SiO_2$—67 mole percent
$BaO$—16.4 mole percent
$B_2O_3$—10 mole percent
$Al_2O_3$—6.6 mole percent.

19. The composition of claim 11 wherein the heat treated barium glass has the following approximate composition:
$SiO_2$—67 mole percent
$BaO$—16.4 mole percent
$B_2O_3$—10 mole percent
$Al_2O_3$—6.6 mole percent.

20. The composition of claim 19 wherein the polymerization initiated is photosensitive.

* * * * *